United States Patent [19]

Granzow, Jr.

[11] 4,098,123

[45] Jul. 4, 1978

[54] METHOD AND APPARATUS FOR MEASURING THE OPERATING TEMPERATURE OF BLOOD WARMING APPARATUS

[75] Inventor: Daniel B. Granzow, Jr., Arlington Heights, Ill.

[73] Assignee: Baxter Travenol Laboratories, Inc., Deerfield, Ill.

[21] Appl. No.: 761,924

[22] Filed: Jan. 24, 1977

[51] Int. Cl.² ............................................. G01K 1/14
[52] U.S. Cl. .................................. 73/343 R; 73/362.8
[58] Field of Search ................. 73/343 R, 349, 339 R, 73/371, 374, 362.8

[56] References Cited

U.S. PATENT DOCUMENTS 3,960,017  6/1976  Romanowski ........................ 73/349

*Primary Examiner*—Richard C. Queisser
*Assistant Examiner*—Joseph W. Roskos
*Attorney, Agent, or Firm*—Henry W. Collins; Paul C. Flattery

[57] ABSTRACT

An apparatus for warming blood and other parental fluids as they are infused through a disposable flow system includes a pair of heating plates which heat the blood as it passes through a warming bag provided in the flow system. One of the heating plates comprises the inside surface of a door pivotally mounted to the apparatus housing, and the other heating plate comprises the underlying surface of the housing so as to form in conjunction with the first plate a user accessable heating chamber for receiving the warming bag. A wedge-shaped temperature-conductive thermometer block having a temperature insulating layer along one surface thereof fits between the heating plates and receives a thermometer to enable the temperature of each heating plate to be independently measured.

8 Claims, 11 Drawing Figures

U.S. Patent  July 4, 1978  Sheet 4 of 4  4,098,123
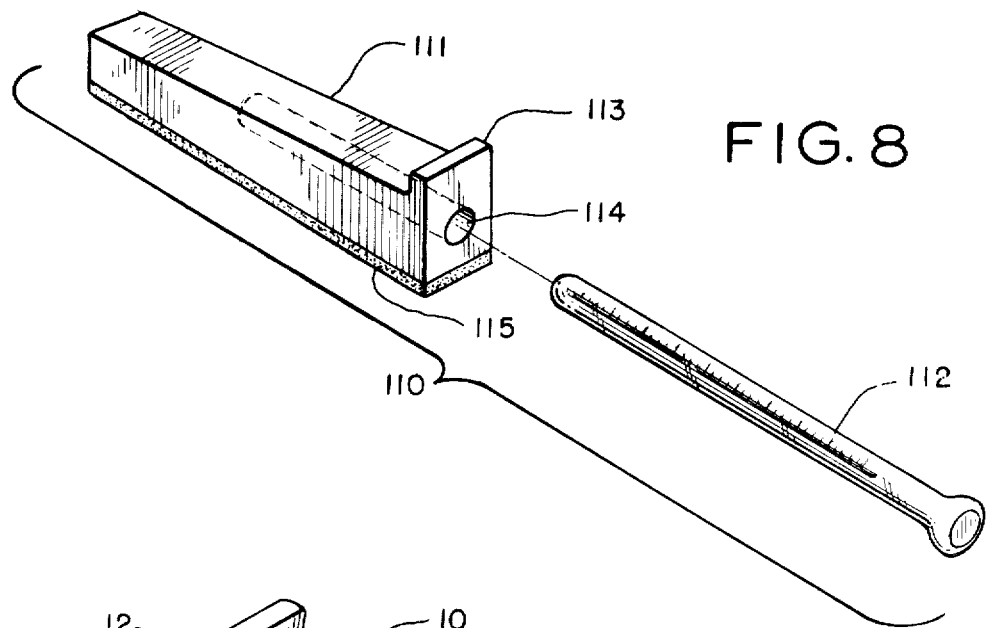
FIG. 8
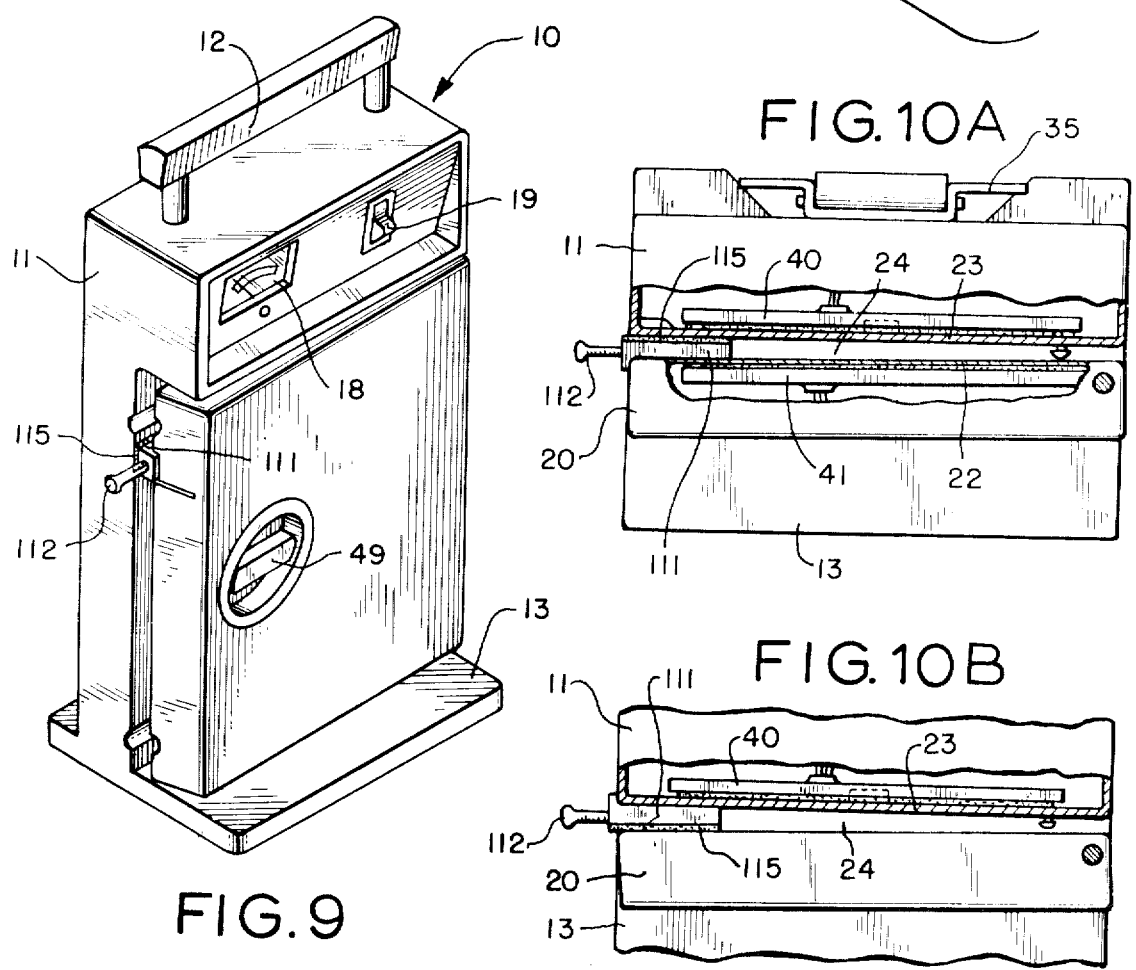
FIG. 10A
FIG. 9
FIG. 10B

METHOD AND APPARATUS FOR MEASURING THE OPERATING TEMPERATURE OF BLOOD WARMING APPARATUS

BACKGROUND OF THE INVENTION

This invention is directed generally to fluid warming apparatus and, more particularly, to a device and method for measuring the operating temperature of apparatus for warming cold parental fluids such as whole blood for intervenous injection or transfusion procedures.

Whole blood is commonly stored in blood banks at a temperature of 4° C until infused into a patient, at which time it is necessary that the blood be warmed to or slightly below the 37° C temperature of the human body if hypothermia and the attendant risk of ventricular fibrillation and cardiac asystole are to be avoided. For applications where substantial and unpredictable quantities of blood are required, as where a patient hemorrages during surgery, it is preferable that blood in storage be transferred substantially directly into the patient, since this avoids warming blood which is not subsequently used.

The apparatus described in the copending application of Robert J. Froehlich and Daniel B. Granzow, Jr., Ser. No. 761,926, concurrently filed herewith, provides an effective and efficient system for dry warming blood or other parental fluids to body temperature during the process of infusing such fluids into the patient. It is a feature of that invention that the temperature of the infused blood is maintained substantially constant at 37° C substantially independent of flow rates, which may vary from 0 to 150 ml per minute depending on the needs of the patient. A further feature is that the operation of the apparatus, as well as the temperature of the blood leaving the apparatus, is continuously monitored, and in the event of a malfunction operation is terminated and an alarm is sounded. Novel self-test provisions within the apparatus allow the operator to verify the operation of these monitoring circuits prior to placing the blood warming apparatus in service.

Sterility of the blood is maintained and contamination of the apparatus is avoided by use of a disposable flow system having a blood warming bag which fits within the apparatus in thermal communication with electric heating elements. An additional feature of that invention provides an alarm in the event of inadvertent removal of the blood processing bag from the apparatus, and AC-coupled sensing circuitry which measures the temperature of the blood at the inlet and outlet portions of the blood processing bag automatically controls the operation of the heating elements to more accurately maintain the output temperature of the blood.

However, the need exists for means to independently measure the operating temperature of such apparatus, both to verify its proper operation, and to facilitate adjustment of its control circuits. Preferably, such temperature measuring means should be convenient and simple to use, and should provide an accurate reading completely independent of the warming apparatus.

Accordingly, it is a general object of the present invention to provide a new and improved method and apparatus for measuring the operating temperature of apparatus for warming blood and other parental fluids prior to infusion into the human body.

It is another object of the present invention to provide a method and apparatus for measuring the operating temperature of apparatus for warming blood and other parental fluids which is simple and convenient to use, and which provides an accurate measurement completely independent of the warming apparatus.

SUMMARY OF THE INVENTION

The invention is directed to temperature measuring apparatus for use in conjunction with a thermometer for measuring operating temperature in fluid warming apparatus of the type which warms fluid as it passes through a disposable warming bag, and which includes a housing defining a heating chamber for containing the warming bag, and a door providing access to the chamber, a first heating plate on the inside surface of the door, and a second heating plate underlying the door. The temperature measuring apparatus comprises a thermally-conductive block member having mounting means for receiving the thermometer and establishing thermal communication therewith, and first and second surfaces on opposite sides thereof, the first surface being adapted to engage in abutting relationship one of the heating planes, and insulating means including a layer of thermally-insulating material on the second surface whereby the block is thermally isolated from the other of the heating plates and the thermometer reads only the temperature of the one plate.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals indentify like elements, and in which:

FIG. 8 is an exploded perspective view of a temperature measurement apparatus constructed in accordance with the invention for adjusting the operation of the blood warmer apparatus;

FIG. 9 is a front perspective view of the blood warmer apparatus showing the placement of the temperature measurement apparatus therein to verify and adjust for proper operation; and FIGS. 10A and 10B are cross-sectional views taken along line 10—10 of FIG. 9 showing the positioning of the temperature measuring apparatus of FIG. 8 to a measure and verify the operation of the housing and door mounted heating elements of the blood warmer apparatus, respectively.

DESCRIPTION OF THE PREFERRED EMBODIMENT

Figure 1:
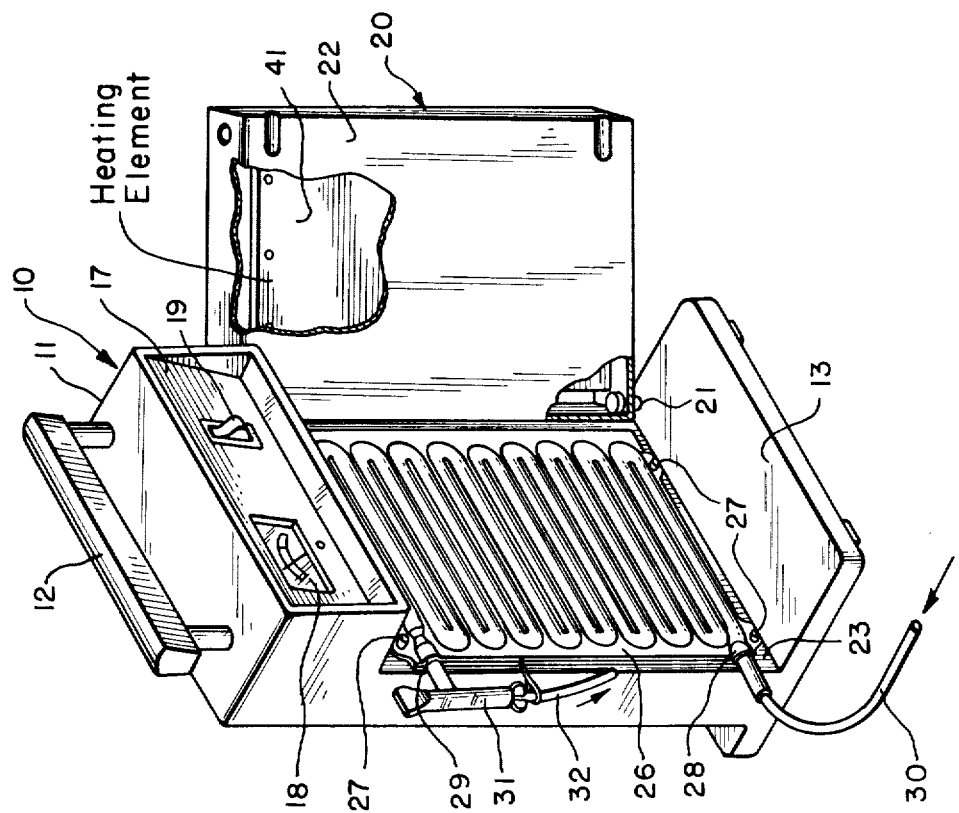
FIG. 1 is a perspective view of a blood warming apparatus constructed in accordance with the invention mounted on a support pole and having a disposable blood warming flow system installed therein.
Figure 2:
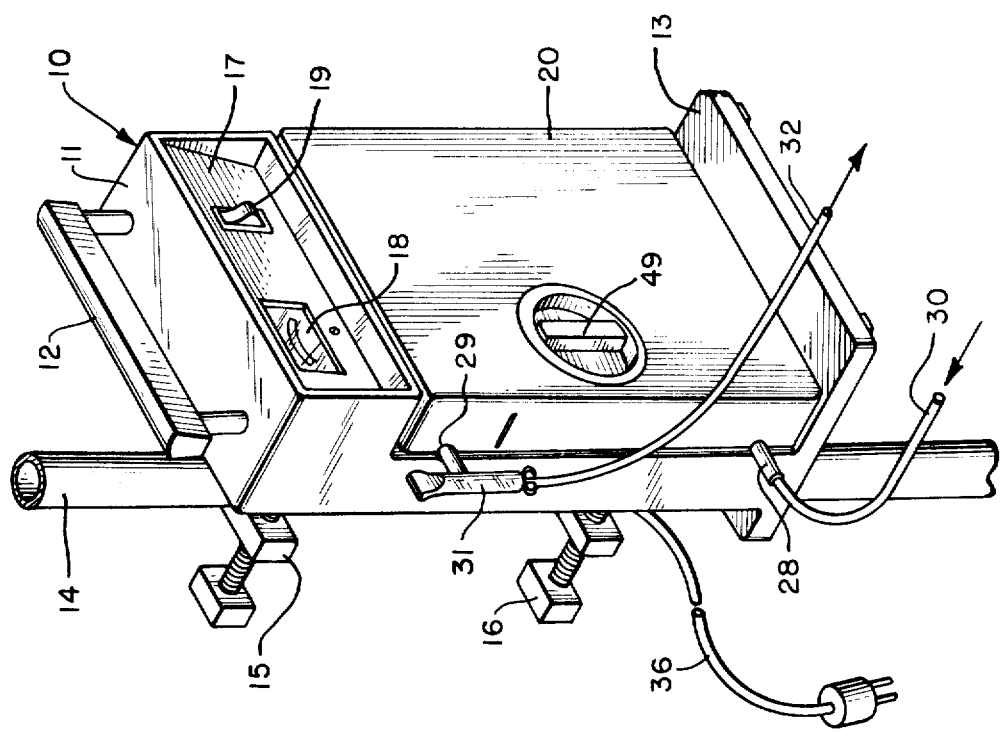
FIG. 2 is a perspective view of the blood warming apparatus set-up on a supporting surface with its heating chamber access door opened and partially broken away to show the internal placement of the blood warming bag of an associated flow system and the location of the heating element within the heating chamber door.
Figure 3:
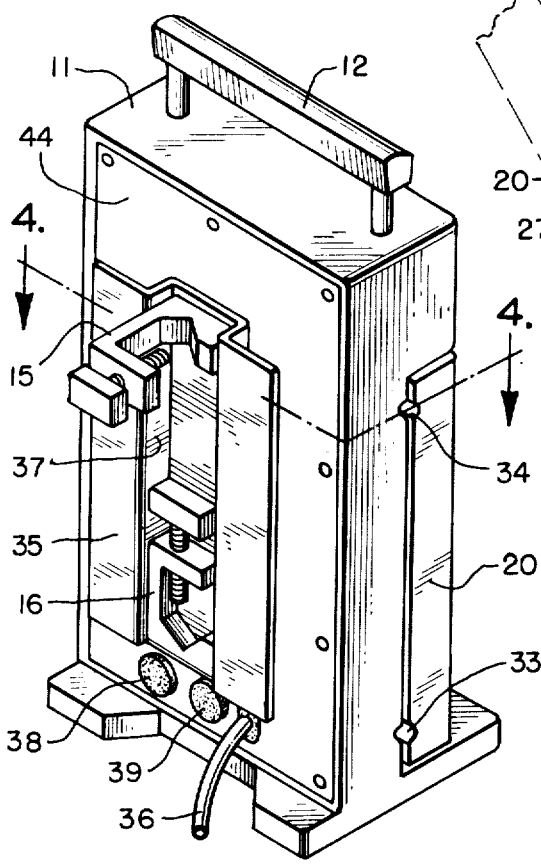
FIG. 3 is a rear perspective view of the blood warming apparatus showing the retractable support clamps and operational test buttons incorporated therein.

Referring to the Figures, and particularly to FIGS. 1-3, a blood warmer apparatus 10 with which the temperature measuring method and apparatus of the invention may be advantageously used is seen to comprise a generally rectangular housing 11 having a handle portion 12 at its top end and a base portion 13 at its bottom end. In use, the blood warmer apparatus can either be set on a flat supporting surface, as in FIG. 2, in which case the wide base portion 13 provides a high degree of stability, or can be mounted on a vertical support or IV pole 14, as in FIG. 1, wherein a pair of clamps 15 and 16 provided on the rear surface of the apparatus provide the necessary stability.

The blood warmer apparatus is also seen to include in the upper portion of its housing a control panel 17, which may be slightly recessed for protection while the apparatus is in transit and storage. The control panel includes temperature indicating means in the form of a meter 18 which is preferably calibrated to provide a direct readout of blood output temperature, and an ON-OFF power switch 19 which allows the operator to initiate and terminate operation of the blood warmer apparatus.

The blood warmer apparatus 10 includes under panel 17 a heater compartment access door 20 which is pivotably mounted on pins 21 (FIG. 2) to housing 11 at one end as to open as shown in FIG. 2, providing access to a heating chamber 24 (FIG. 4) formed within the blood warmer apparatus between the inside wall or plate 22 of the door 20 and the underlying wall or plate 23 of housing 11.

Blood warmer apparatus 20 is intended for use in conjunction with a sterile disposable fluid flow system through which whole blood to be warmed is caused to flow, either by means of gravity, pressure or pump feed, to a patient or other utilization means. One such flow system is marketed by Fenwal Laboratories, a division of Travenol Laboratories, Inc., of Deerfield, Ill., U.S.A., as model No. 4C2416, and is intended for use with a blood administration set for infusing blood from a storage container directly to a patient. The flow system includes a flat generally rectangular warming bag 26 (FIG. 2) which is suspended within chamber 24 by means of a plurality of support pins 27. The warming bag 26 is internally baffled to define a tortuous flow path 25 (FIG. 5) for the blood as it flows from an inlet port 28 at the lower end of the bag to an outlet port 29 at the upper end of the bag. Inlet port 28 is connected by a length of tubing 30 to a container of refrigerated blood (not shown), and outlet port 29 is connected through a chamber 31 and a length of tubing 32 to a needle adapter (not shown), to which a needle is attached for venipuncture. When access door 20 is closed as shown in FIG. 1, the blood warming bag 26 is sandwiched between plate 22 of door 20 and plate 23 of housing 11. When the door 20 is closed connection is established to inlet and outlet ports 28 and 29 through recesses 33 and 34, respectively, provided along the edges of the door and housing. These recesses allow the door to be closed snugly over the warming bag.

Referring to FIG. 3, housing 11 is seen to include on its rear surface a wing-shaped plate 35 which forms a convenient reel around which the power cord 36 of the apparatus can be wound during storage. Bracket 35 also defines an open channel 37 on the rear surface into which clamps 15 and 16 pivot when not in use. Also contained on the rear surface are a pair of push button switches 38 and 39, which when depressed provide first and second tests of the safety monitoring circuits of the blood warmer apparatus.

Figure 4:
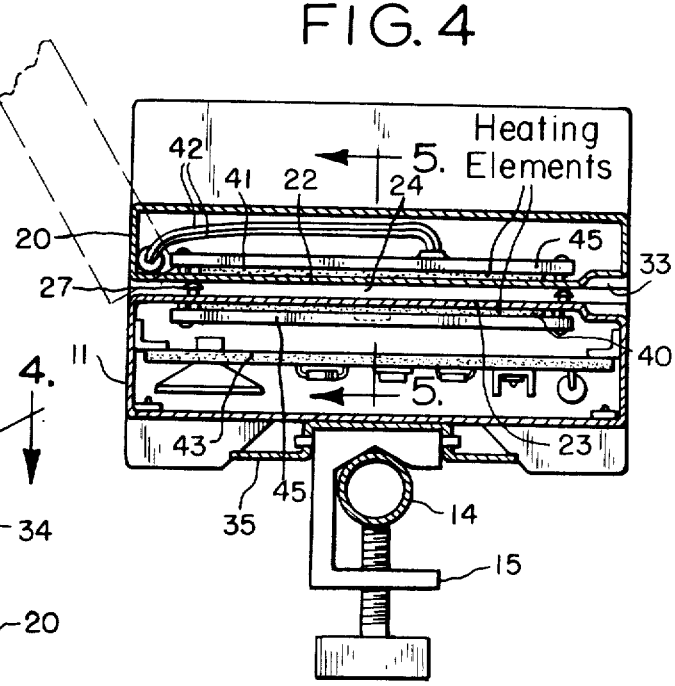
FIG. 4 is a cross-sectional view taken along line 4—4 of FIG. 3 showing the interior construction of the apparatus and the utilization of the support clamps for mounting the apparatus to a supporting pole.

Referring to FIG. 4, to warm the blood flowing through warming bag 26 the blood warming apparatus includes a first heating element 40 within housing 11 in substantially contiguous contact with the inside surface of plate 23. A second heating element 41 is positioned within door 20 immediately behind and adjacent to the inside 22 of the door. The two heating elements are held in position by relatively thick and inflexible plates 45 of insulating material. Electrical power is supplied to this heating element by means of electrical conductors 42 which extend into the interior of housing 11 through the upper pivot hinge 21 (FIG. 6) of door 20. Electrical components and circuitry including a printed wiring board 43 necessary for operation of the blood warmer apparatus 10 are contained within housing 11 behind heating element 40. These items are readily accessible for adjustment and repair by removing the rear plate 44 of housing 11.

Figure 6:
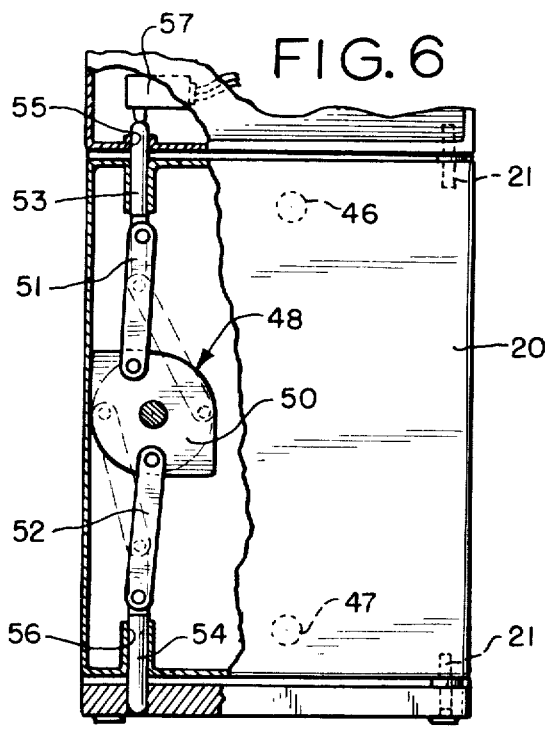
FIG. 6 is a fragmentary front elevational view of the blood warmer apparatus partially broken away to show the construction and operation of the heating chamber access door latch assembly.
Figure 5:
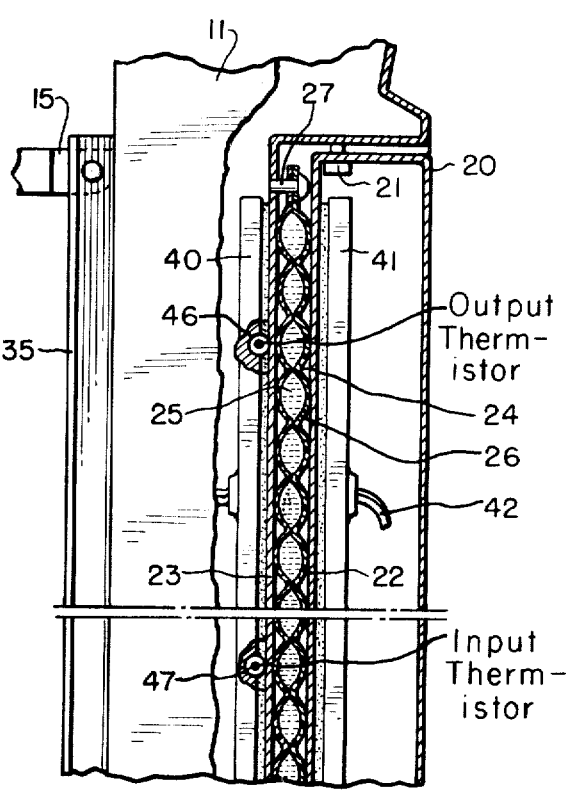
FIG. 5 is a cross-sectional view taken along line 5—5 of FIG. 4 showing the placement and construction of the heating elements of the heater apparatus and the placement of the input and output blood temperature sensing elements provided therein.

Referring to FIG. 5, when access door 20 is closed blood warming bag 26 is sandwiched between plates 22 and 23 so that blood flowing through the interior passageways 25 of the warming bag comes into thermal communication with heating elements 40 and 41. The temperature of the blood flowing through the blood warming bag 26 is sensed by temperature sensing means in the form of a pair of thermistors 46 and 47 located on the center line of recess 24 near the top and bottom of the recess, as shown in FIGS. 5 and 6. Thermistor 47 measures the temperature of the blood flowing through the warming bag near inlet ports 28, and thermistor 46 measures the temperature of the blood in bag 26 near outlet port 29. Within the blood warming apparatus termistors 46 and 47 provide signals indicative of the temperature of the blood discharged from the apparatus as well as the differential temperature which exists between the blood entering the apparatus and the blood being discharged. This information is utilized by control circuitry within the apparatus to control the operation of heating elements 40 and 41, and consequently the temperature to which the blood is heated.

To lock door 20 in a closed position a latch assembly 48 is provided. This assembly includes a user-actuable handle 49 on the outside surface of the door which drives a bell-crank 50 located within the door. The bell-crank is connected by linkages 51 and 52 to locking pins 53 and 54 located on the top and bottom edges of the door. When handle 49 is turned from the extreme counterclockwise position shown to an extreme clockwise position locking pins 53 and 54 are retracted from engagement with aligned recesses 55 and 56 in housing 11 and door 20 is free to open.

When door 20 is locked in its closed position locking pin 53 engages the actuator pin of a switch 57 within housing 11. This switch in conjunction with associated circuitry functions to provide an alarm should the user attempt to unlatch the door while the blood warming apparatus is in operation. To this end switch 57 is arranged so as to be actuated only when locking pin 53 is fully extended so that the alarm will be sounded as the user first attempts to turn handle 49 and before the locking pins have become disengaged from their recesses in housing 11.

Figure 7:
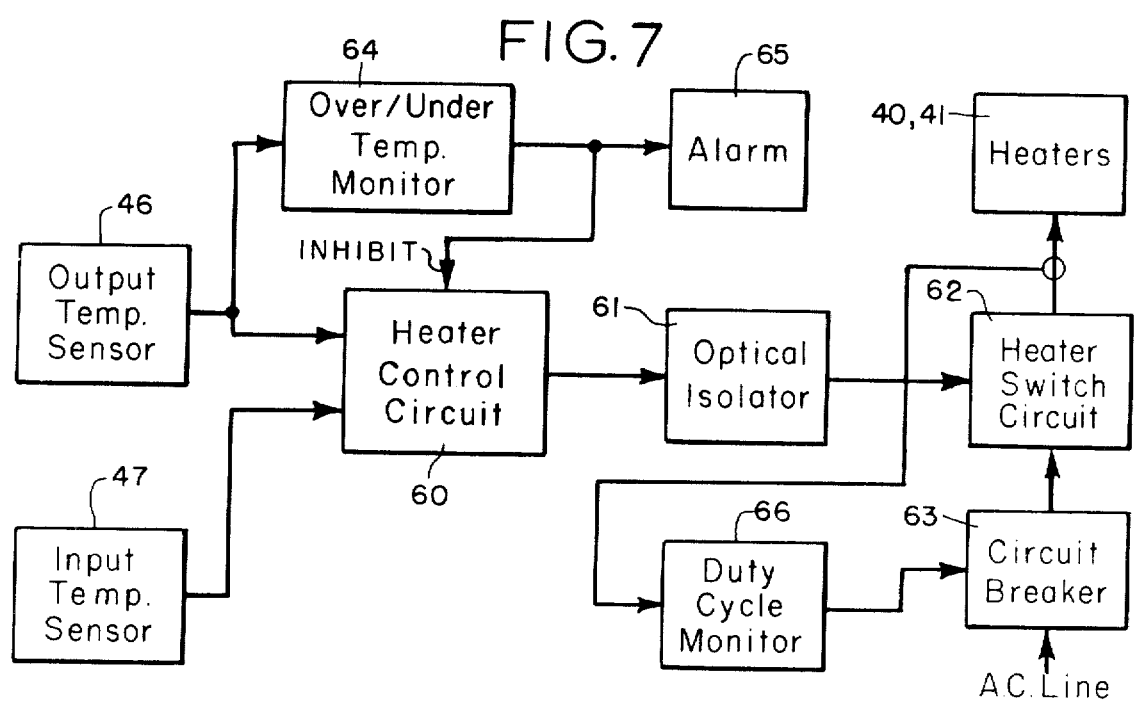
FIG. 7 is a simplified functional block diagram of the blood warmer apparatus showing the principal functional elements thereof.

Referring to FIG. 7, the temperature of the blood discharged from the blood warming apparatus 10 is controlled by means of a heater duty cycle control circuit 60 which causes the heating elements 40 and 41 to be periodically energized with a duty cycle dependent on the temperatures sensed by thermistors 46 and 47. The output of this circuit, which comprises a heater on-off control signal, is applied through an optical isolator 61 to a heater switch circuit 62, which controls application of current to heater elements 40 and 41. Current for powering heater 40 and 41 is supplied to heater switch circuit 62 from the AC line through a circuit breaker 63 which also functions as a user-actuable power switch and a means of automatically disconnecting power to the unit in the event of a malfunction. Optical isolator 61, which comprises a conventional commercially available component, functions to electrically isolate duty cycle control circuit 60 from the switched AC line and the other control circuits of the blood warming apparatus to minimize leakage between the AC line and the patient under treatment.

The heater duty cycle control circuit 60 varies the duty cycle of heaters 40 and 41 both as a function of the output temperature sensed by sensor 46, and as a function of the differential between the input and output temperature of the blood as sensed by sensors 46 and 47. As the output temperature of the blood increases beyond the desired level control circuit 60 functions to reduce the duty cycle of heaters 40 and 41, thus lowering the output temperature to the desired level. Conversely, as the output temperature of the blood decreases below the desired level control circuit 60 functions to increase the duty cycle of the heaters, thus increasing the blood temperature to the desired level. At the same time, should the differential in sensed temperatures increase, signifying an increase in blood flow rate, the duty cycle of heaters 40 and 41 is automatically increased to compensate for the increased flow rate and avoid the output temperature of the blood falling below the desired level. Conversely, as the difference between the sensed input and output temperatures decreases, signifying a reduced flow rate, the duty cycle of the heaters is automatically reduced to avoid heating the blood beyond the desired level.

Protection is provided against malfunction of the control circuit by means of a first alarm circuit comprising an over-under temperature monitor circuit 64 which provides an output in the event that the blood output temperature, as sensed by sensor 46, rises above a predetermined maximum temperature or falls below a predetermined minimum temperature. In practice, the maximum temperature limit is set just slightly above the nominal body temperature to 37° C to avoid any possibility of damage to the blood being processed, and the minimum temperature limit is set at approximately 0° C so as to sense a failure of the output temperature sensor 46.

In the event of an output from temperature monitor 64 indicating either an over or under temperature condition, an alarm 65 is actuated to indicate to the user that a malfunction has occurred. Simultaneously, the application of control signals from control circuit 60 to the heater switch circuit 62 is interrupted to prevent further heating of the blood by heating elements 40 and 41.

The blood warming apparatus 10 incorporates a second monitoring circuit 66 which monitors current supplied to heating elements 40 and 41. During normal operation this current is periodically switched on and off at a rate determined by control circuit 60. Should a malfunction occur which results in a continuous current being applied to heaters 40 and 41, duty cycle monitor 66 generates an output signal which is applied to an appropriate terminating device in circuit breaker 63 to interrupt power to the blood warming apparatus. In practice, duty cycle monitor 66 is constructed to terminate operation whenever power to the heating elements is not interrupted in a 3 second interval.

A further feature of the control arrangement shown in FIG. 7 is that power to the heating element is switched on only during those portions of the applied AC line current when that current is passing through its zero axis. This is done to minimize transients which would otherwise be generated by switching during periods of current flow through the heating elements, and to minimize the attendant radio frequency interference produced as a result of such transients.

In accordance with the invention, the accuracy of the temperature indicated by meter 18 and the operation of the heating elements can be independently confirmed by inserting a temperature measurement apparatus 110 in the heating chamber 24 of the heating apparatus. Referring to FIG. 8, this apparatus includes a thermally-conductive block member 111 and temperature measuring means in the form of a thermometer 112. The block member 111 is preferably rectangular in cross section, and wedge-shaped to provide interfaces with plates 22 and 23 when inserted into heating compartment 24 with the door partially open, as shown in FIG. 12. In practice, this is done with the blood warming apparatus positioned horizontally with winged plate 35 resting on a supporting surface, so that the thermometer block 111 and thermometer 112 will more readily remain in position. A flange portion 113 at the outside or wider end of the block member facilitates positioning the block within the heating chamber, and an aperture 114 is provided at this end for receiving thermometer 112, which may comprise a standard generally cylindrical oral thermometer. Alternatively, an electronic or other type of thermometer could be used, with an appropriate modification to aperture 114 if necessary.

To enable the thermometer block member 111 to selectively measure the temperature of either the door heating plate 22 or the base heating plate 23, the block member is preferably provided with a layer of heat-insulating material 115 along one face thereof. As shown in FIG. 10A, when this insulating layer is positioned toward plate 23 thermometer 112 reads the temperature of the heating plate 22 associated with door 20, whereas when the insulating layer is positioned toward plate 22, as shown in FIG. 10B, thermometer 112 reads the temperature of plate 23 associated with housing 11.

In a successful embodiment of the invention the thermometer block was formed of aluminum with an overall length of 2.5 in. and a width of 0.5 in., and tapered from a thickness at its narrow end of 5/16 in. to a thickness at its wide end of 7/16 in., excluding flange portion 113. Aperture 114 was formed with a diameter of 3/16 in. for receiving a standard oral thermometer. Layer 115 was formed of sponge rubber with a thickness of ⅛ inch. In practice a period of approximately 3 minutes may be required to alow a stabilized output reading when using an oral thermometer.

Temperature measurement apparatus 110 provides a simple and convenient means for ascertaining the proper operation of blood warming apparatus 10 since it is merely necessary to position the warming apparatus on its back and insert the measurement block within the door. This ease of use enables the operation of the warming apparatus to be frequently checked by relatively unskilled operators. Furthermore, since the measurement is taken completely independently of the warming apparatus, the resulting temperature reading may be taken as an absolute indication of proper operation prior to actual use of the warming apparatus.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. Temperature measuring apparatus for use in conjunction with a thermometer for measuring operating temperature in fluid warming apparatus of the type which warms fluid as it passes through a disposable warming bag, and which includes a housing defining a heating chamber for containing the warming bag, and a door providing access to the chamber, a first heating plate on the inside surface of the door, and a second heating plate underlying the door, said temperature measuring apparatus comprising, in combination:
 a thermally-conductive block member having mounting means for receiving said thermometer and establishing thermal communication therewith, and first and second surfaces on opposite sides thereof, said first surface being adapted to engage in abutting relationship one of said heating plates; and
 insulating means including a layer of thermally-insulating material on said second surface whereby said block is thermally isolated from the other of said heating plates and said thermometer reads only the temperature of said one plate.

2. Temperature measuring apparatus as defined in claim 1 wherein said door is pivotally mounted to said housing, and said block member is generally wedge-shaped whereby said first and second surfaces are substantially parallel to said first and second heating plates, respectively, when said door is closed on said block.

3. Temperature measuring apparatus as defined in claim 2 wherein said thermometer is generally cylindrical in form, and said mounting means comprise an aperture in the wider end of said block dimensioned to slidably receive said thermometer.

4. Temperature measuring apparatus as defined in claim 3 wherein said block member includes a flange portion at the wider end thereof for positioning said block adjacent the edge of said door when said door is closed on said block.

5. Temperature measuring apparatus for measuring operating temperature in fluid warming apparatus of the type which warms fluid as it passes through a disposable warming bag, and includes a housing, a door pivotally mounted to the housing providing access to the chamber, a first heating plate on the inside surface of the door, and a second heating plate underlying the door and forming in conjunction with the first heating plate the heating chamber, said temperature measuring apparatus comprising, in combination:
 a thermometer;
 a generally wedge-shaped thermally-conductive block member having mounting means at the wider end thereof for receiving said thermometer and establishing thermal communication therewith, and first and second ramp surfaces on opposite sides thereof adapted to be substantially parallel to respective ones of said first and second heating plates when said door is closed down on said block member; and
 insulating means including a layer of thermally-insulating material on one of said surfaces whereby said block is thermally isolated from the corresponding one of said heating plates and said thermometer reads the temperature of only the other one of said heating plates.

6. Temperature measuring apparatus as defined in claim 5 wherein said thermometer is generally cylindrical in form, and said mounting means comprise an aperture in the wider end of said block dimensioned to slidably receive said thermometer.

7. Temperatures measuring apparatus as defined in claim 6 wherein said bock member includes a flange portion at the wider end thereof for positioning said block adjacent the edge of said door when said door is closed on said block.

8. A method for measuring the operating temperature of a desired heating plate in a fluid warming apparatus of the type which warms fluid as it passes through a disposable warming bag, and which includes a housing defining a heating chamber for containing the warming bag, and a door mounted to the housing providing access to the chamber, a first heating plate on the inside surface of the door, and a second heating plate underlying the door and providing in conjunction with the first heating plate the heating chamber, said method comprising the steps of:
 inserting a thermometer in the wider end of a wedge-shaped thermally-conductive block having first and second opposing ramp surfaces, and a thermally insulating layer overlying said second ramp surface;
 positioning the block between the heating plates with said first ramp surface facing said desired one of said heating plates; and
 closing the door on the heating block to bring said first ramp surface into contact with said desired heating plate and said second ramp surface into contact with said other heating plate whereby said thermometer reads only the temperature of said desired heating plate.

* * * * *